United States Patent
Prozzo

(10) Patent No.: US 6,737,650 B2
(45) Date of Patent: May 18, 2004

(54) INFRARED EMITTER, ITS MANUFACTURE, AND PROCESS FOR USING

(75) Inventor: Christopher D. Prozzo, Athens, VT (US)

(73) Assignee: Bacharach, Inc., New Kensington, PA (US)

(*) Notice: Subject to any disclaimer, the term of this patent is extended or adjusted under 35 U.S.C. 154(b) by 128 days.

(21) Appl. No.: 09/872,336

(22) Filed: Jun. 1, 2001

(65) Prior Publication Data

US 2002/0005486 A1 Jan. 17, 2002

Related U.S. Application Data

(60) Provisional application No. 60/209,164, filed on Jun. 2, 2000.

(51) Int. Cl.$^7$ ............................................. G01N 21/61
(52) U.S. Cl. .................................................. 250/343
(58) Field of Search ....................................... 250/343

(56) References Cited

U.S. PATENT DOCUMENTS 3,694,624 A * 9/1972 Buchta .................... 250/495.1
5,369,277 A * 11/1994 Knodle et al. ............. 250/343

* cited by examiner

*Primary Examiner*—Constantine Hannaher
(74) *Attorney, Agent, or Firm*—Webb Ziesenheim Logsdon Orkin & Hanson, P.C.

(57) ABSTRACT

Using at least one surface mount resistor as an infrared light emitter in an analytical instrument provides low cost, long life and high reliability.

3 Claims, 1 Drawing Sheet

INFRARED EMITTER, ITS MANUFACTURE, AND PROCESS FOR USING

REFERENCE TO RELATED APPLICATION

This application is based on a provisional application Serial No. 60/209,164 which was filed Jun. 2, 2000.

BACKGROUND OF THE INVENTION

Analytical instruments which utilize infrared absorbence to determine the presence of, or concentration of, a compound or compounds, require a source of infrared light in order to perform analysis. This source, referred to henceforth as an IR (infrared) emitter, typically takes the form of a wire, filament or conductive ceramic element. To activate, the IR emitter is heated by passing electric current through the conductive wire, filament or ceramic element. The current is converted to heat according to the formula that the square of the electrical current multiplied by the "emitter's" resistance is equal to the heat emitted. The infrared emission is proportional to the temperature and surface area of the heated element. Often, it may be desirable or necessary to pulse the infrared emission by interrupting the electrical current periodically to modulate the surface temperature of the element.

Commercially available IR emitters typically suffer one or more of the following shortcomings: high cost; short life; mass may be too high for pulsing; poor mechanical stability; long lead times; and fragility. Packaging may inhibit efficient collection of emissions. They are usually not adjustable by the user. And the resistance to get effective IR emission may be too low to provide efficient drive circuitry.

OBJECTS OF THE INVENTION

It is an object of this invention to overcome the shortcomings of the IR emitters currently being used commercially. Specifically, it is an object of this invention to provide an IR emitter that is relatively easy to use and to control by the user and which provides accurate, reproducible results.

SUMMARY OF THE INVENTION

The objects are accomplished by employing a surface mount resistor, commonly used as a heat supplier, as an IR emitter for use in analytical instruments.

BRIEF DESCRIPTION OF THE INVENTION

Surface mount resistors are fabricated by depositing a conductive layer on the surface of a ceramic substrate with metal contacts on either end. The temperature of the conductive surface is proportional to the power dissipated by the resistor. Since the substrate is ceramic (a thermal insulator) and the mass of the conductive layer is relatively small, the surface temperature can easily be modulated by pulsing the electric current through it.

Figure 1:
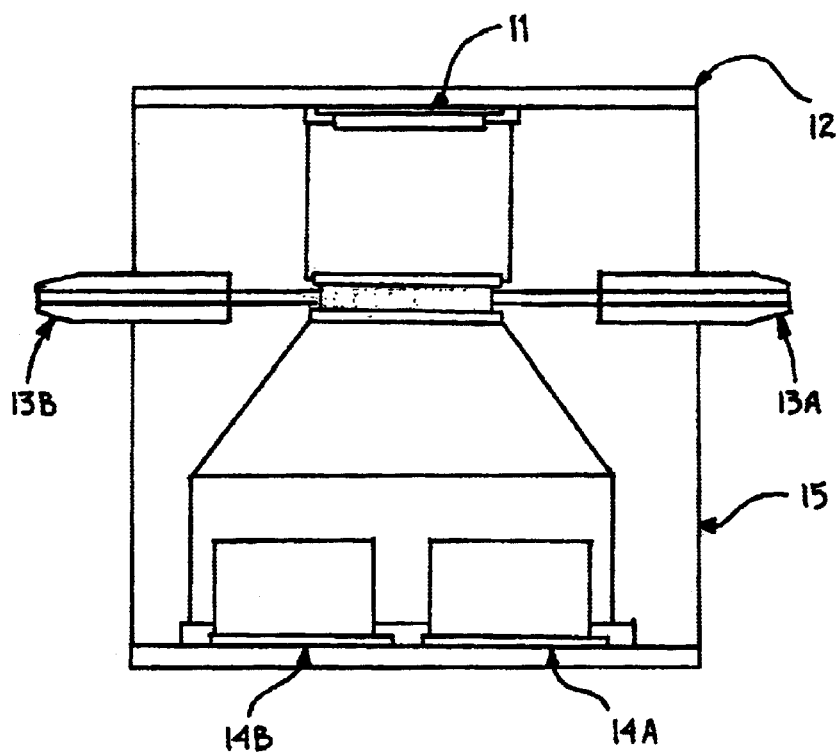

Of the many different types of surface mount resistors available, several are ideally suited to perform in analytical applications such as Panasonic ERA Series metal film chip resistors and ERJ Series thick film chip resistors. The use of a surface mount resistor as an IR emitter for use in a typical gas cell is shown in FIG. 1. In FIG. 1, the gas cell 15, comprises the resistor circuit board 12 containing the resistor layer 11. The gas enters at the inlet port 13A and departs at the outlet port 13B. Infrared light emitted from the resistor 11 passes through the gas to the detectors 14A & 14B which is adapted to detect the intensity of the light within a specific wavelength range that represents a particular component and where the intensity represents the concentration of that component of the gas composition.

The surface mount emitter displays the following advantages over the commercially available emitters:

Ultra low cost (pennies each);

Long life and high reliability;

Low mass for pulsing;

Excellent mechanical stability;

Off the shelf availability;

Ruggedness;

User determines optimal packaging by PCB layout of a single resistor or as an array of resistors;

Series and/or parallel combinations permit surface area and resistance adjustments; and they are Available in virtually any resistance required.

Figure 2:
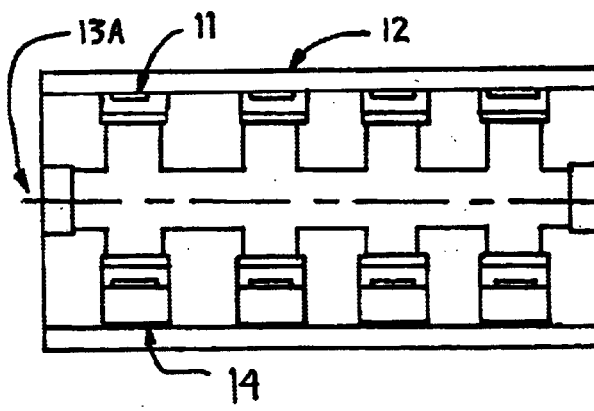
Figure 2A:
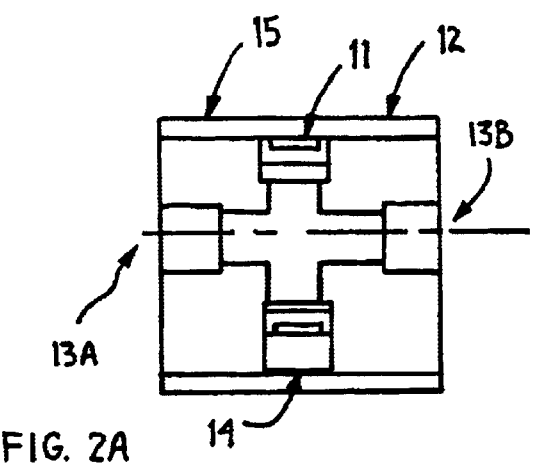

Because of their flexibility and low cost, multi-sensor systems can afford to employ a separate IR emitter for each detection channel as shown in FIGS. 2 and 2A.

Fabrication of custom surface mount emitter arrays is easily done using standard PCB design tools; and their assembly can be automated as with any surface mount PCB.

The operating temperature of the surface mount resistor is relatively low compared to the filaments and ceramic heaters used in commercially available emitters. However, higher temperatures and/or higher efficiency necessary in some analytical applications can be obtained by placing them in closer proximity to the IR detector or the IR emitter element can be employed as an array of emitters to maximize surface area of emission.

What is claimed is:

1. An analytic instrument comprising:

a gas cell having a gas inlet port for introducing a gas into the cell and a gas outlet port for exhausting the gas from the cell;

a surface mount resistor disposed in the cell, the surface mount resistor including a conductive layer deposited on an insulating substrate that has on opposite ends thereof contacts in contact with the conductive layer, the surface mount resistor responsive to an electric current passing through the conductive layer for emitting light; and a detector disposed in the cell in spaced relation with the surface mount resistor defining a gap therebetween through which the gas moves in the cell from the inlet port to the outlet port, the detector detecting an intensity of light emitted from the surface mount resistor after passing through the gap.

2. The instrument of claim 1, further including a printed circuit board disposed in the cell with the surface mount resistor mounted thereon.

3. The instrument of claim 1, further including a plurality of surface mount resistors connected in parallel or some combination of series and parallel.

* * * * *